United States Patent
Liu et al.

(10) Patent No.: US 7,483,735 B2
(45) Date of Patent: Jan. 27, 2009

(54) APPARATUS AND METHOD FOR MONITORING BODY COMPOSITION BY MEASURING BODY DIELECTRIC CONSTANT AND BODY IMPEDANCE BASED ON THE METHOD OF FREQUENCY DIGITAL SAMPLING

(75) Inventors: Yan Liu, Shenzhen (CN); Gang Jing, Shenzhen (CN); Jian Wu, Shenzhen (CN); Yuye Jin, Shenzhen (CN); Guanping Feng, Shenzhen (CN); Yueqiu Li, Shenzhen (CN)

(73) Assignee: Research Institute of Tsinghua University, Shenzhen (CN)

( * ) Notice: Subject to any disclaimer, the term of this patent is extended or adjusted under 35 U.S.C. 154(b) by 252 days.

(21) Appl. No.: 10/727,677

(22) Filed: Dec. 4, 2003

(65) Prior Publication Data

US 2004/0113636 A1 Jun. 17, 2004
US 2004/0196054 A9 Oct. 7, 2004

(30) Foreign Application Priority Data

Dec. 14, 2002 (EP) .................................. 02028205

(51) Int. Cl.
*A61B 5/05* (2006.01)
*A61B 5/04* (2006.01)
*G01N 27/00* (2006.01)
*G01R 27/00* (2006.01)
*G01R 27/08* (2006.01)

(52) U.S. Cl. ...................... 600/547; 600/554; 324/71.1; 324/600; 324/693; 324/698; 324/709; 324/712; 324/717

(58) Field of Classification Search ................. 600/547, 600/554; 324/71.1, 600, 693, 698, 709, 712, 324/717
See application file for complete search history.

(56) References Cited

U.S. PATENT DOCUMENTS

| 4,291,708 | A | * | 9/1981 | Frei et al. | 600/547 |
| 4,860,753 | A | * | 8/1989 | Amerena | 600/306 |
| 5,579,782 | A | * | 12/1996 | Masuo | 600/547 |
| 5,611,351 | A | * | 3/1997 | Sato et al. | 600/547 |
| 5,720,296 | A | * | 2/1998 | Cha | 600/554 |

(Continued)

FOREIGN PATENT DOCUMENTS

EP    1 080 686 A1    3/2001

(Continued)

*Primary Examiner*—Max Hindenburg
*Assistant Examiner*—Jeffrey G Hoekstra
(74) *Attorney, Agent, or Firm*—Westman, Champlin & Kelly, P.A.

(57) ABSTRACT

A method for measuring dielectric constant of body endermic tissues and body impedance based on the method of frequency digital sampling and for evaluating body composition is provided, inputting the method through the I/O interface of a microprocessor the measured body weight frequency signals, oscillating frequency signals related to dielectric constant of body endermic tissues and body impedance signals corresponding to non-fixed different frequencies, and calculating through the software of the microprocessor the body fat content, total body water, ratio between intracellular water and total body water. The body weight, body fat content, total body water and ratio between intracellular water and total body water are displayed on the display. A body composition monitor based on the above method, which includes a weighing sensor, a weighing signal processing circuit, and a display unit.

11 Claims, 13 Drawing Sheets

U.S. PATENT DOCUMENTS

| | | | |
|---|---|---|---|
| 6,369,337 B1 * | 4/2002 | Machiyama et al. | 177/25.13 |
| 6,473,643 B2 * | 10/2002 | Chai et al. | 600/547 |
| 6,487,445 B1 * | 11/2002 | Serita et al. | 600/547 |
| 6,532,824 B1 * | 3/2003 | Ueno et al. | 73/780 |
| 2003/0149375 A1 * | 8/2003 | Chen | 600/547 |

FOREIGN PATENT DOCUMENTS

| | | |
|---|---|---|
| EP | 1 147 740 A1 | 10/2001 |
| WO | WO 01/36952 A1 | 5/2001 |
| WO | WO 02/080770 A1 | 10/2002 |

* cited by examiner

APPARATUS AND METHOD FOR MONITORING BODY COMPOSITION BY MEASURING BODY DIELECTRIC CONSTANT AND BODY IMPEDANCE BASED ON THE METHOD OF FREQUENCY DIGITAL SAMPLING

The present application claims priority of European patent application Serial No. 02028205.9, filed Dec. 14, 2002.

FIELD OF THE INVENTION

The present invention relates to measurement devices in general, and more particularly to a body composition monitor apparatus which measure dielectric constant of body tissues under the skin and body impedance based on the method of frequency digital sampling.

BACKGROUND OF THE INVENTION

Body composition refers to the total contents consisting of every tissue and organ of a human's body, its total weight is namely body weight, which is composed of two parts: fat and non-fat content. The former mass is called body fat mass, the ratio between it and body mass is called percent body fat (Fat %) in human body. The latter includes the weight of water, viscera, bones, muscle, mineral salts and so on, and is also called lean body mass or fat free mass, among which water content accounts for most of the mass. 70% fat content is mainly distributed in and below the region of the waist.

Body composition indicates the rates of lean body mass (LBM) and body fat. Different tissue body structure contents result in different body functions and activity, and in order to maintain the body's normal functions, it is required that all contents adjust to one another at certain rates. Once the maladjusted rates destroy the normal physiological functions and activity, the normal growth and health of the body will be affected. Body composition can also indicate physical attributes, body shape characteristic and body stature, and fat content can indicate body fitness. So body composition is significant to make the fitness standard and body shape assessment and so on.

There are already some methods for measuring body fat content alone, such as isotope dilution method, underwater weighing method, height and weight empirical algorithms, ultrasound measurement, infrared measurement and so on. All these methods have the shortcomings of complicated equipment and inconvenient operation.

There are three indices for measuring body water content: total body water (TBW), intracellular water (ICW) and extracellular water (ECW). TBW equals the sum of ICW and ECW, and these three indices are significant to assess the physical attributes and the balance status of intracellular and extracellular liquid. There are also corresponding methods for measuring body water. The method often used is drug dilution method. For example, to take certain doses of antibilin or $D_2O$, after these medical substances disperse uniformly to global body, to extract some sample of blood and urine for testing. Also there is a method called multiple-factor isotope dilution, which can measure multiple body contents including water content from microcosmic aspect. None of these methods presented above can meet the demand of fast and integrated monitoring of body weight, fat and water content. Especially some methods of medical substance dilution, can only be done in hospitals, have long time period, cost much and can not be done as often as needed.

The method of bioelectrical impedance analysis (BIA) is considered to be the simplest method for measuring human body composition (such as fat content). This method is based upon the principle that body tissue conductivity of bio electricity in different areas of the body stimulated by outside electricity is different. For example, the conductivity of muscle is high and then the impedance is small because of its high rate of water content, while the conductivity of fat tissue, bone tissue and lung tissue filled with air is very low and the impedance is relatively great. So body composition can be estimated according to tissue's impedance. Up to now, though those open patents on measuring body composition based on bioelectrical impedance analysis (BIA) adopt different circuits, arithmetic, apparatus structures and different output methods, they have three common characteristic in nature. The first is to obtain bioelectric impedance by measuring voltage or voltage difference then transforming to digital value through A/D, the second is to use at least more than three electrodes (groups), among which two electrodes is certain to apply high frequency small current to human body in order to stimulate bio electricity and the other two electrodes collect stimulated voltage signal indicating bioelectrical impedance, if unite two of four electrodes to be used as reference electrodes, then there are 3 electrodes, the third is that the different frequency signals applied to human body must be signals with determined frequencies. As disclosed in U.S. Pat. No. 6,151,523, bioelectrical impedance can be measured by placing electrodes at a person's toes and heels, and by inputting the weight and height of the subject, percent body fat can also be estimated. The shortcomings of the above methods are: first, the methods have limitation if body fat and water content are determined based on bioelectrical impedance alone, second, because of the great diversity of human bodies, if only one or multiple determined frequencies are applied to human body, the results can not indicate body status accurately, and third, there are large errors in such low-cost apparatus when using voltage measurement to determine body impedance.

OBJECTS OF THE INVENTION

The present invention aims to solve those questions above. The object is to provide a method for measuring dielectric constant of body tissues under the skin by using capacitance sensor contacting body skin and based on the method of frequency digital sampling.

The present invention also aims at providing a method according to which, human body is connected with oscillator circuit as a two end impedance element, then generates unfixed frequencies related to body impedance, and by sampling frequency, the digital signal, the body impedance is determined.

The present invention also aims to provide a method of determining body composition by jointly using measurement of two parameters: dielectric constant of body tissues under the skin and body impedance.

The present invention also aims to provide a body composition monitor for measuring body dielectric constant and body impedance based on the method of frequency digital sampling, and the monitor is used to monitor body composition in everyday life.

SUMMARY OF THE INVENTION

The object set out above are achieved by a method according to claim 1 and a body composition monitor according to claim 6 respectively.

The present invention includes two kinds of measuring modes and corresponding apparatus for composition monitoring. The first mode is to assemble the measuring unit and display unit in an integrative apparatus. The apparatus includes feet-on electrode plates and capacitance grid sensor, both of which are attached to the platform of weighing scale, body impedance and water measuring circuits, weighing sensor, weighing signal process circuit, microprocessor system, display, keyboard, and so on. Before measurement, the subject's gender, height and age are input by keyboard. The measuring results including body weight, fat content, water content and so on are shown on the display. The second mode is measuring unit and display unit are separated as measuring apparatus and display apparatus physically. The measuring apparatus includes feet-on electrode plates and capacitance grid sensor, both of which are attached to the platform of weighing scale, weighing sensor, infrared signal emitting and receiving circuit, microprocessor system, body impedance and water test circuit, weighing signal process circuit and so on. The display apparatus consists of infrared signal emitting and receiving circuit, microprocessor system, display, keyboard and so on. Before measurement, the subject's gender, height and age are input by keyboard of display apparatus. Measuring apparatus emits the results of weight, fat content, water content by infrared signal transmitting circuit to display apparatus hand-held or hung up on wall, and the results are shown on display.

Because the dielectric constant of body tissues under the skin is related directly to the fat content and water content of body tissues, the present invention regards the dielectric constant of body tissues under the skin as a measuring parameter for evaluating body composition. The present invention's method and principle for measuring dielectric constant of body tissues under the skin are: when a testee stands barefoot on the measuring platform, the soles of the testee two feet contact two capacitance grid sensors, and the oscillator circuit connected with the capacitance grid sensors generates oscillating frequency signals related to the dielectric constant of body tissues under the skin. The signals are sampled and then the dielectric constant of the body tissues under the skin can be obtained.

Because body impedance is related directly to the fat content and water content of body tissues, the present invention regards the body impedance as a measuring parameter for evaluating body composition. The present invention's method and principle for measuring body impedance is: when a testee stands with barefoot on the measuring platform, his two feet contact two (groups of) electrode plates mounted on the platform simultaneously and respectively. At this time human body is connected with oscillator circuit as a two ends impedance element and a loop is formed at and below human's waist region. The oscillating frequency of the oscillator circuit is related to the impedance of human body. By changing parameters of other elements of oscillator circuit, several different frequency signals are obtained related to body impedance, then the body impedances corresponding to several different frequencies are determined.

The method and principle of the present invention to determine body composition by jointly using measurement of the two kinds of measuring parameters, dielectric constant of body tissues under the skin and body impedance, is to introduce math models the dielectric constant of body tissues under the skin, the body impedance, body weight obtained from weighing sensor and circuit, and the input data by keyboard, to calculate by microprocessor, and to display body weight, body fat content, total body water (TBW) and the ratio between intracellular water and TBW (ICW/TBW) by display.

The math models for calculating these data are as follows:

$$Fat = \frac{a_1 H + a_2 W + a_3 R_{m1} + a_4 R_{m2} + a_5 R_{m3} + a_6 Y + a_0}{ce^{-(b_1 H + b_2 W)}}$$

$$Fat(\%) = \frac{Fat}{W}$$

$$TBW = \frac{Fat + K_1 \varepsilon_r}{K_2 \varepsilon_r} + K_3$$

where W is body weight (Kg), Rm1, Rm2, Rm3 are body impedance corresponding respectively to three kinds of undetermined frequencies. $\varepsilon_r$ is the dielectric constant of body tissues under the skin; Fat is body fat value (kg); Fat (%) is percent body fat; H is body height (cm); Y is a subject's age, $a_0, a_1, a_2, a_3, a_4, a_5, a_6, b_1, b_2, c, K1, K2, K3, K4$ are all coefficients, whose values are related to gender. Among these parameters, W, Rm1, Rm2, Rm3, $\varepsilon_r$ are determined by measurement, H, Y and gender are input by keyboard.

DETAILED DESCRIPTION OF THE PREFERRED EMBODIMENT

Figure 1A:
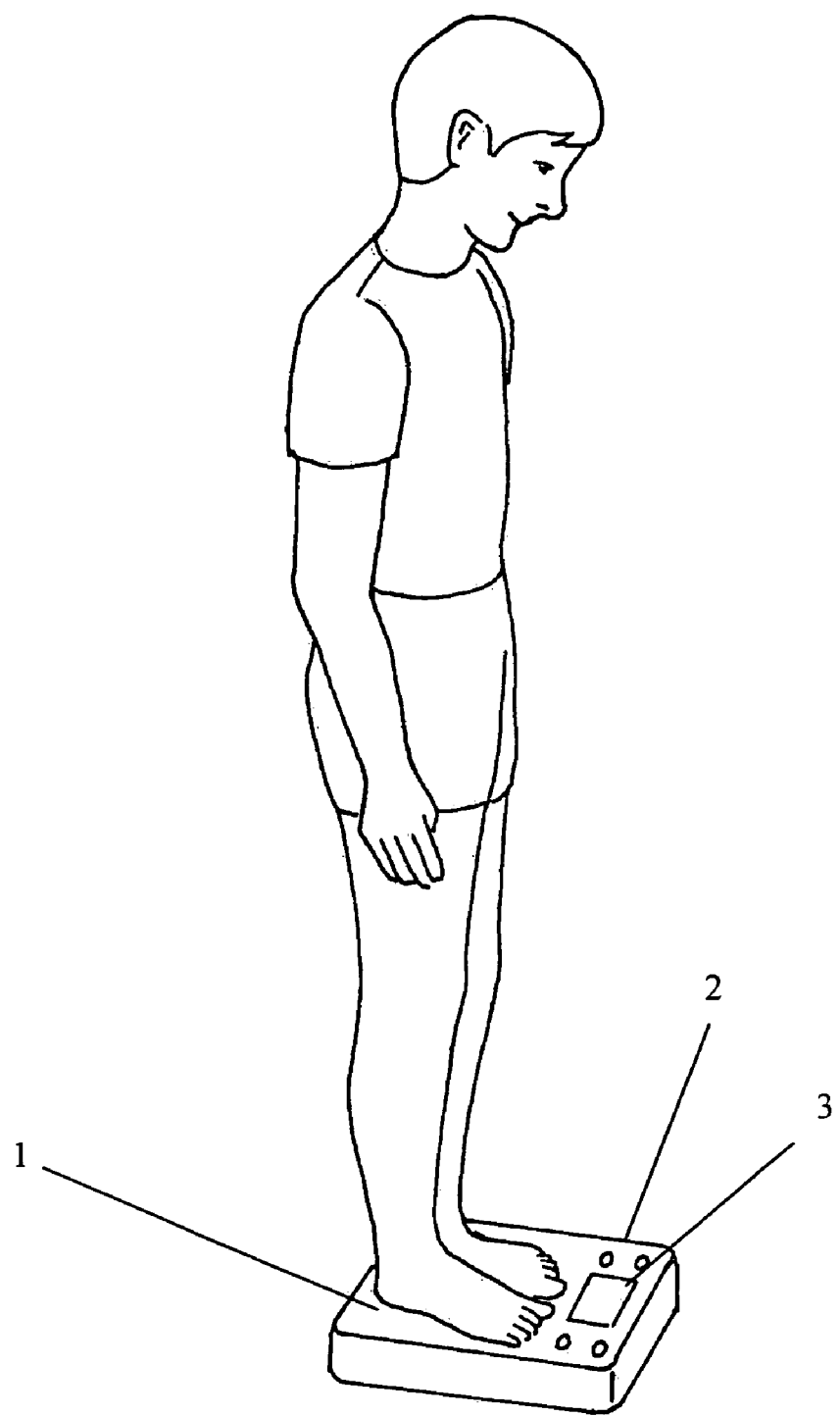
FIG. 1A is a schematic view showing the mode of assembling the function units of measuring and displaying body composition in an integrative apparatus.

Referring now to FIG. 1A, The first measuring mode is to assemble the measuring function unit and display function unit into a integrative apparatus. A testee stands with barefoot on the platform 1 of the integrative apparatus attaching feet-on electrode plates and capacitance grid sensor. The testee's data are input by keyboard 2 of the integrative apparatus. The determined results by measurement including weight, fat content and water content are shown on display 3.

Figure 1B:
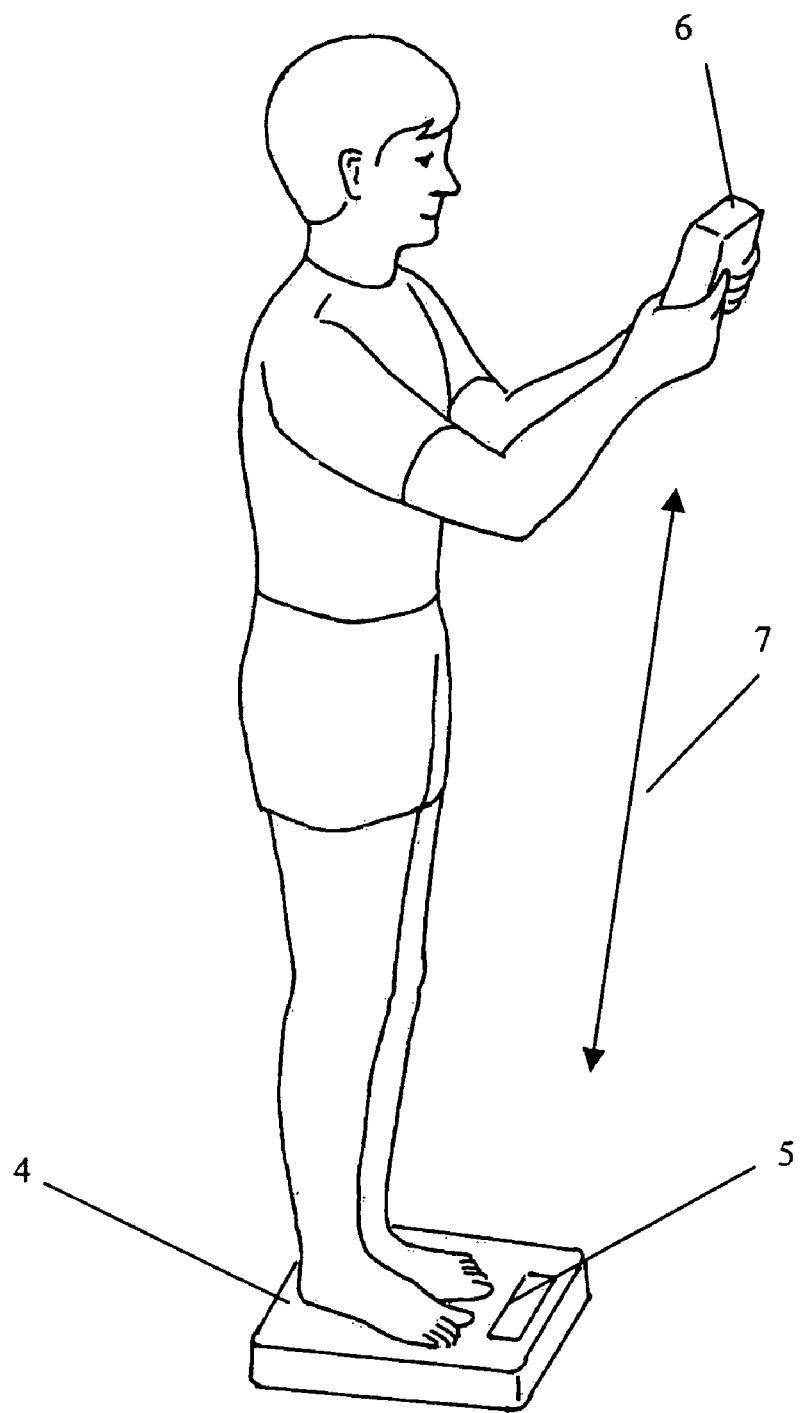
FIG. 1B is a schematic view showing the mode of separating the function units of measuring and displaying body composition to measuring apparatus and display apparatus physically.

Referring now to FIG. 1B, The second mode is that the measuring function unit and display function unit are separated as measuring apparatus and display apparatus physically. There are microprocessors in both the measuring apparatus and display apparatus, and data are transmitted between the two apparatus by the transmitting manner of infrared 7. A testee stands with barefoot on the platform 4 of measuring apparatus attaching foot-on electrode plates and capacitance grid sensor. The testee's data are input by display apparatus 6 held in hand by the testee. Measuring apparatus emits determined data including body weight, body fat ratio and body water ratio in infrared 7 transition manner through window 5 to display apparatus and then these data are shown here.

There are two embodiment examples of the measuring platform configuration of the integrative apparatus in the present invention.

Figure 2A:
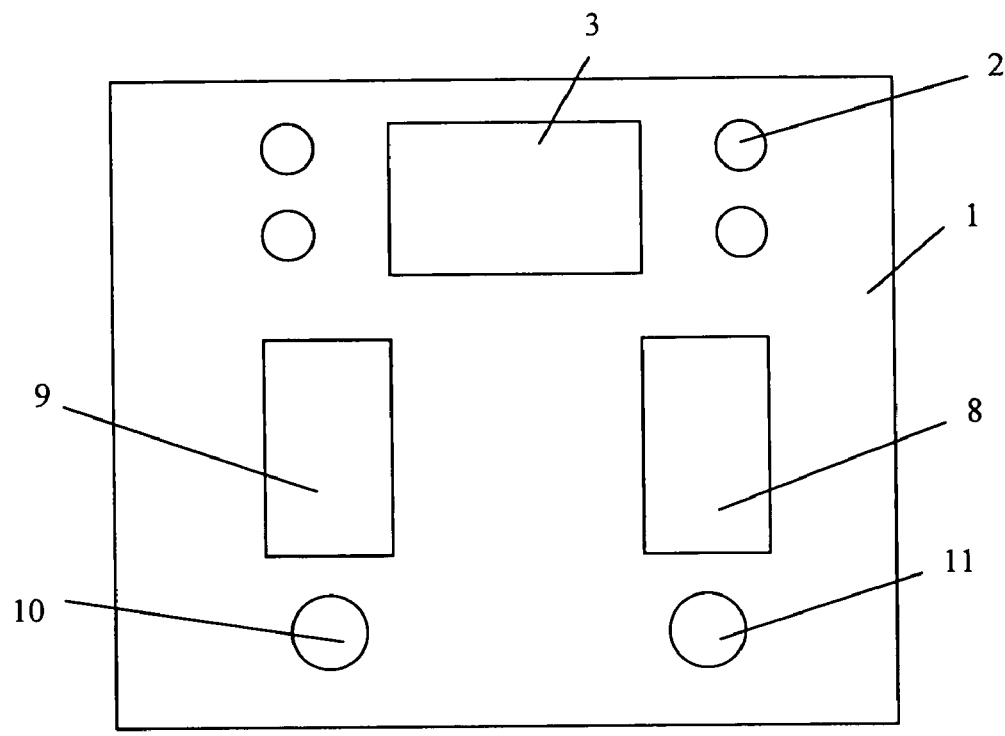
FIG. 2A shows an embodiment example of measuring platform configuration of the integrative apparatus based on the mode shown in FIG. 1A.

Referring now to FIG. 2A, it shows a kind of measuring platform configuration of integrative apparatus based upon the measuring mode shown in FIG. 1A. The platform 1 is positioned on scale sensor. The surface of the platform 1 is insulative and, there are two electrodes 8, 9 on the platform, which have enough area to be contacted by human's sole and are made of conductive materials. There is no conduction between electrodes 8 and 9, between electrodes 8, 9 and platform 1. Also on the platform 1 there is at least more than one capacitance grid sensors 10, 11, which are used to measure the dielectric constant of body tissues under the skin and can be contacted by human's soles. Keyboard 2 and display 3 are located on platform 1.

Figure 2B:
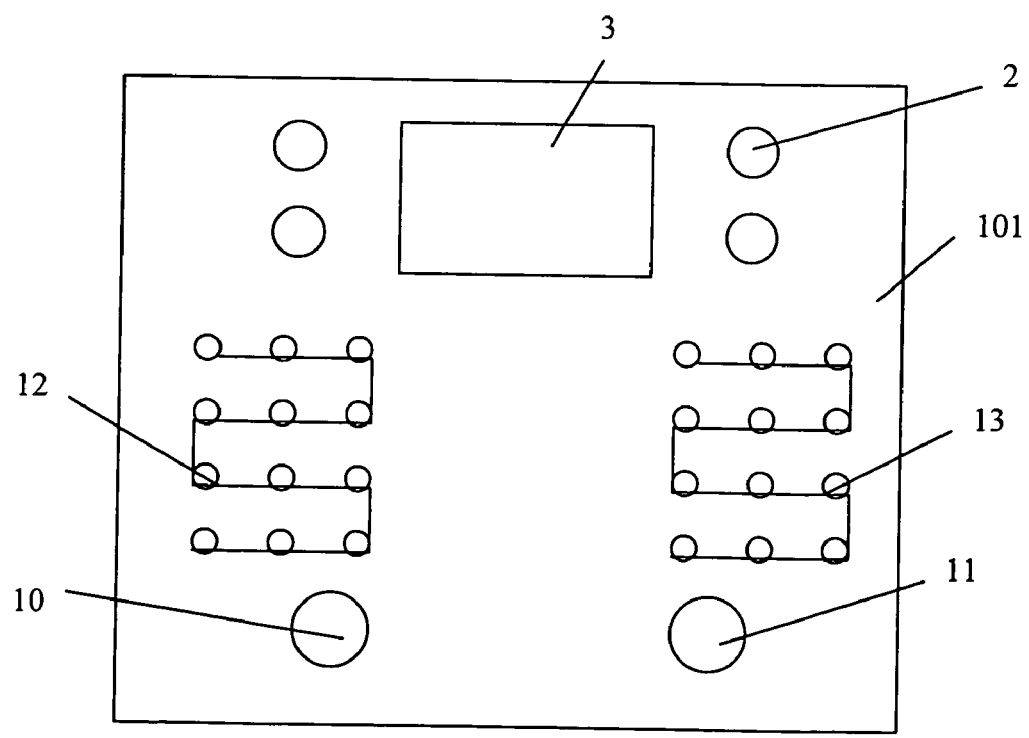
FIG. 2B shows an alternative embodiment example of measuring platform configuration of the integrative apparatus based on the method shown in FIG. 1A.

Referring now to FIG. 2B, it shows another kind of measuring platform configuration of integrative apparatus based upon the measuring mode shown in FIG. 1A. The platform 101 is positioned on scale sensor. The surface of the platform 101 is insulative, and there are two electrodes 12, 13 comprising electrode plates connected by conducting wires on the platform 101. There is no conduction between electrodes 12 and 13, between electrodes 12,13 and platform 101. Also on the platform there are at least one or more capacitance grid sensors 10, 11, which can be contacted by human's soles. Keyboard 2 and display 3 are located on platform 101.

Figure 3A:
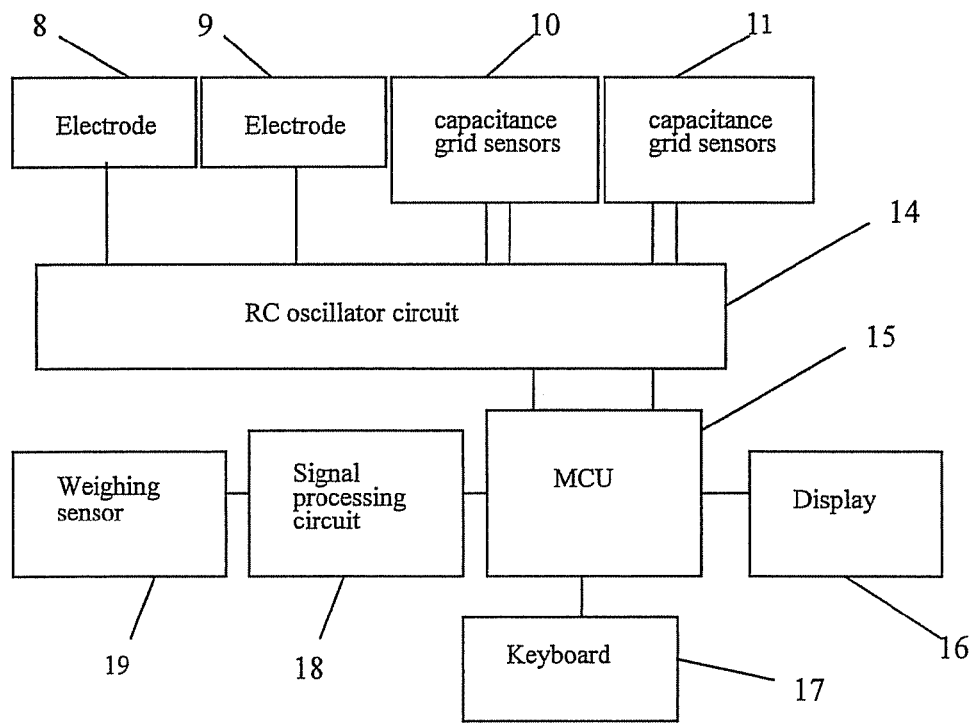
FIG. 3A shows the system configuration based on the integrative apparatus shown in FIG. 2A.
Figure 3B:
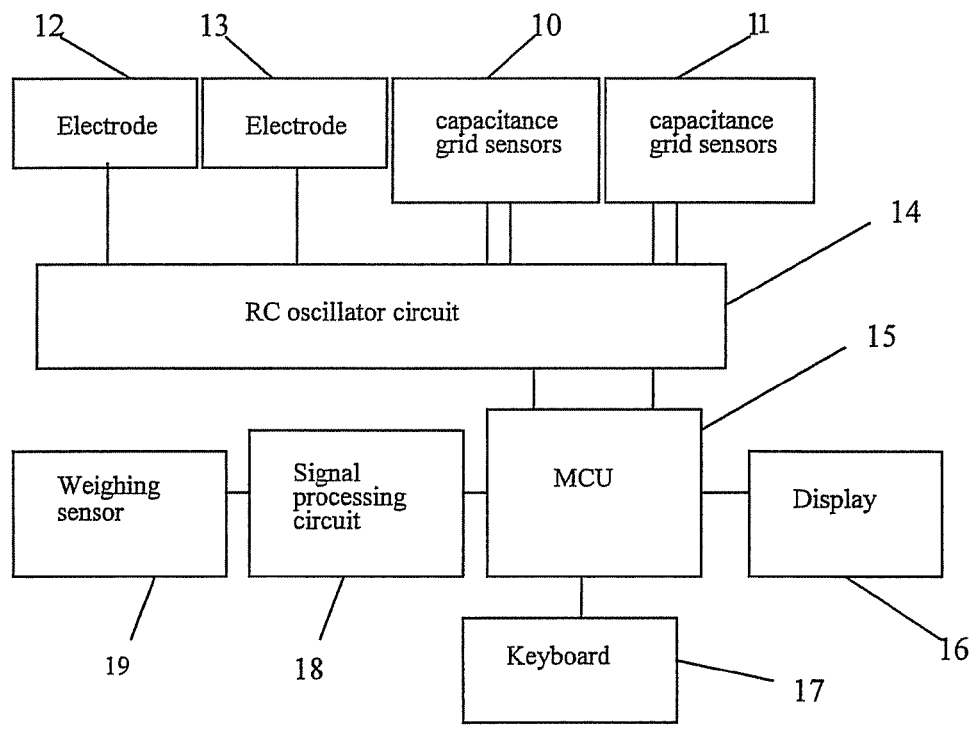
FIG. 3B shows the system configuration based on the integrative apparatus shown in FIG. 2B.

Referring now to FIG. 3A, it shows the system configuration of integrative apparatus shown in FIG. 2A. Electrode plates 8, 9 and capacitance grid sensors 10, 11 are connected with the interfaces of positive feedback RC oscillator circuit 14 for measuring the dielectric constant of body tissues under the skin and body impedance, and positive feedback RC oscillator circuit 14 for measuring the dielectric constant of body tissues under the skin and body impedance is connected with two interfaces of microprocessor (MCU) system 15 of the integrative apparatus. One of the two interfaces is a signal collection interface of MCU system 15 of the integrative apparatus, the other is a control interface of MCU system 15 of the integrative apparatus used to send switch instruction to positive feedback RC oscillator circuit 14 for measuring the dielectric constant of body tissues under the skin and body impedance in order to switch undetermined multiple frequencies and measuring signals of the dielectric constant of body tissues under the skin. The signal wires of weighing sensor 19 are connected with weighing signal process circuit 18 and the processed signal is applied to one interface of the MCU system 15 of the integrative apparatus as a frequency signal through weighing signal processing circuit 18. Display 16 is connected with the output of MCU system 15 of the integrative apparatus and is used to show the input data and the measuring result. Keyboard 17 is connected with the I/O interface of MCU system 15 of the integrative apparatus and is used to input data to MCU system 15 of the integrative apparatus. Referring now to FIG. 3B, it shows the system configuration of integrative apparatus shown in FIG. 2B. The two groups of electrode 12, 13 composed of electrode plates connected with one another by wires and being able to contact human's soles, and capacitance grid sensor 10, 11 are connected with the interfaces of positive feedback RC oscillator circuit 14 for measuring the dielectric constant of body tissues under the skin and body impedance, and positive feedback RC oscillator circuit 14 for measuring the dielectric constant of body tissues under the skin and body impedance is connected with two interfaces of MCU system 15 of the integrative apparatus. One of the interfaces is the signal collection interface of MCU 15 system of the integrative apparatus and the other is a control interface of the MCU system 15 of the integrative apparatus used to send switch instruction to positive feedback RC oscillator circuit 14 for measuring the dielectric constant of body tissues under the skin and body impedance in order to switch undetermined multiple frequencies and the measuring signal of body dielectric constant of tissues under the skin. The signal wires of weighing sensor 19 are connected with weighing signal process circuit 18, and the processed signal is applied to one interface of MCU system 15 of the integrative apparatus as a frequency signal through weighing signal processing circuit 18. Display 16 is connected with the output of MCU system 15 of the integrative apparatus and is used to show the input data and the measuring results. Keyboard 17 is connected with the I/O interface of MCU 15 and is used to input data to MCU 15.

Figure 4A:
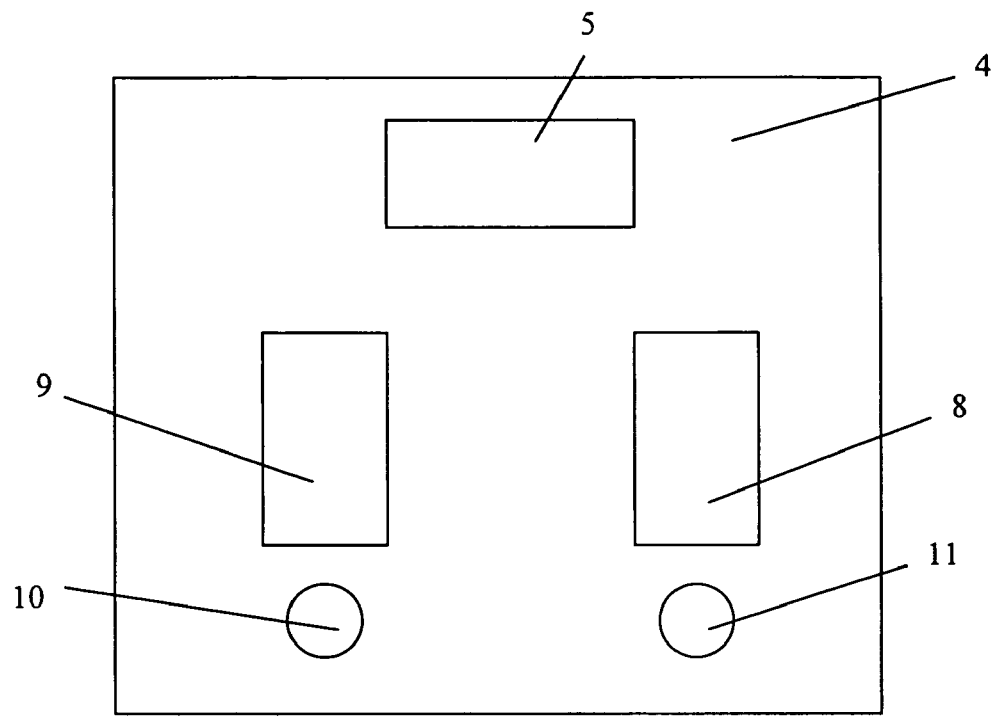
FIG. 4A shows an embodiment example of measuring platform configuration of measuring apparatus based on the mode shown in FIG. 1B.

Referring now to FIG. 4A, it shows a kind of measuring platform configuration of measuring apparatus based upon the measuring mode shown in FIG. 1B. The platform 4 is positioned on scale sensor, and on the platform 4, there are two electrodes 8, 9 with enough area to be contacted by human's sole. Also on the platform 4 there are at least one or more capacitance grid sensors 10, 11 which can be contacted by human's soles and are used to measure dielectric constant of the body tissues under the skin. Infrared ray transmitting window 5 is positioned on measuring platform 4.

Figure 4B:
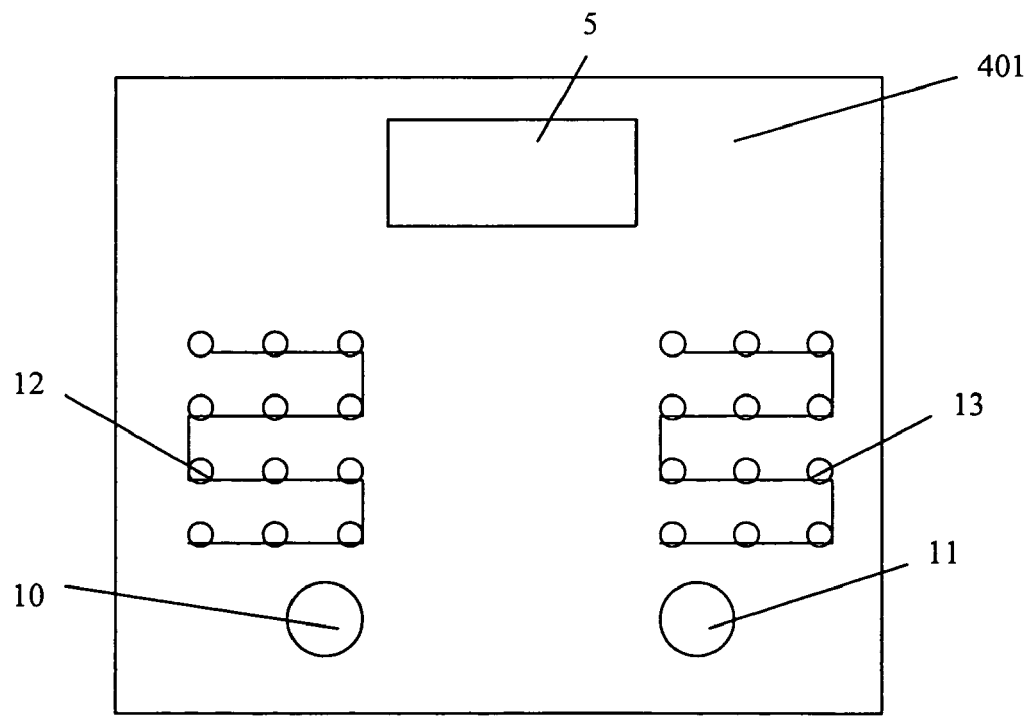
FIG. 4B shows an alternative embodiment example of measuring platform configuration of measuring apparatus based on the mode shown in FIG. 1B.

Referring now to FIG. 4B, it shows another kind of measuring platform configuration of measuring apparatus based upon the measuring mode shown in FIG. 1B. The platform 401 is positioned on scale sensor, and on the platform 401, there are two groups of electrode 12, 13 comprising electrode plates connected by conducting wires and with enough area to be contacted by human's soles. Also on the platform 401 there are at least one or more capacitance grid sensors 10, 11 which can be contacted by human's soles and are used to measure dielectric constant of the body tissues under the skin. Infrared ray transmitting window 5 is positioned on measuring platform 401.

Figure 5A:
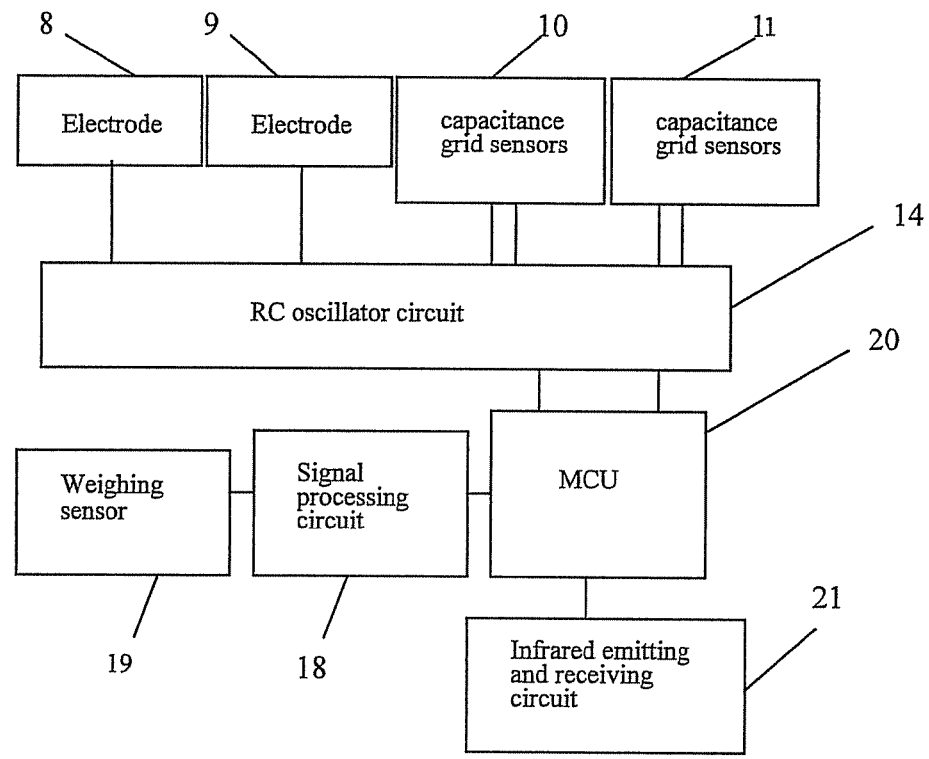
FIG. 5A is a schematic view showing the system configuration based on the measuring apparatus shown in FIG. 4A.

Referring now to FIG. 5A, it shows the system configuration of measuring apparatus shown in FIG. 4A. Electrodes 8, 9 and capacitance grid sensor 10, 11 are connected with the interfaces of positive feedback RC oscillator circuit 14 for measuring the dielectric constant of body tissues under the skin and body impedance, and positive feedback RC oscillator circuit 14 for measuring the dielectric constant of body tissues under the skin and body impedance is connected with two interfaces of microprocessor MCU system 20 of measuring apparatus. One of the two interfaces is a signal collection interface of MCU system 20 of measuring apparatus, the other is a control interface of MCU system 20 of measuring apparatus used to send switch instruction to positive feedback RC oscillator circuit 14 for measuring the dielectric constant of body tissues under the skin and body impedance in order to switch undetermined multiple frequencies and measuring signal of dielectric constant of body tissues under the skin. The signal wires of weighing sensor 19 are connected with weighing signal process circuit 18, and the processed signal is applied to one interface of MCU system 20 of the measuring apparatus as a frequency signal through weighing signal processing circuit 18. The determined data by measurement are emitted or received by infrared ray-emitting-receiving circuit 21.

Figure 5B:
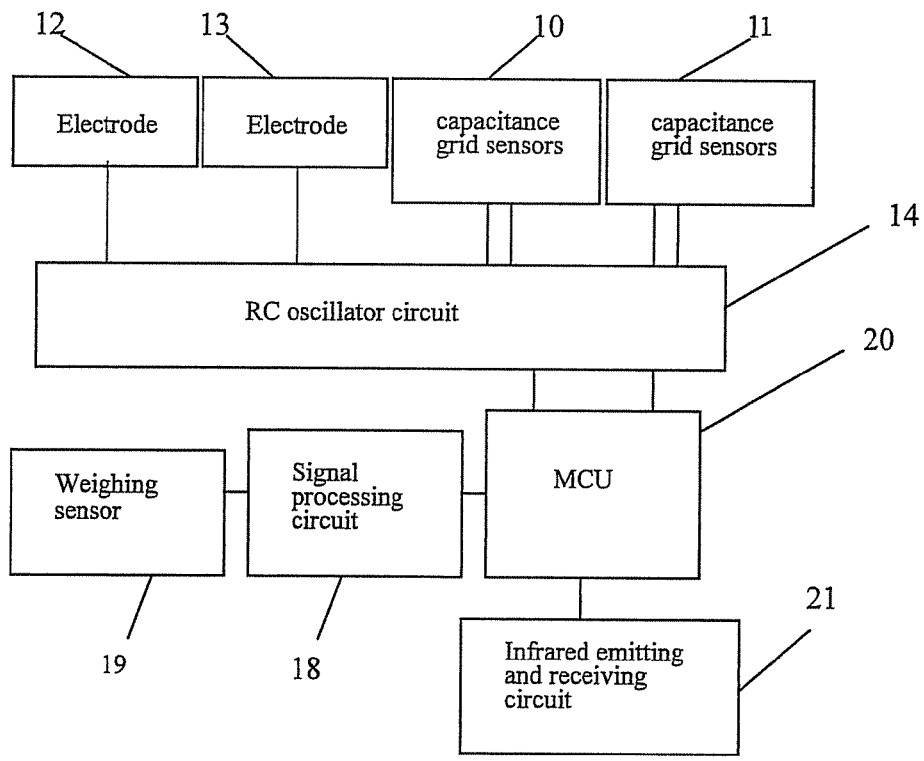
FIG. 5B is a schematic view showing the system configuration based on the measuring apparatus shown in FIG. 4B.

Referring to FIG. 5B, it shows the system configuration of measuring apparatus shown in FIG. 4B. Two groups of electrodes 12, 13, which are composed of electrode plates connected with one another by wires and can be in contact with human's soles, and capacitance grid sensors 10, 11 are connected with the interfaces of positive feedback RC oscillator circuit 14 for measuring the dielectric constant of body tissues under the skin and body impedance, and positive feedback RC oscillator circuit 14 for measuring the dielectric constant of body tissues under the skin and body impedance is connected with two interfaces of MCU 20 system of the measuring apparatus. One of the interfaces is the signal collection interface of MCU 20 system of the measuring apparatus and the other is a control interface of MCU system 20 of the measuring apparatus used to send switch instruction to positive feedback RC oscillator circuit 14 for measuring the dielectric constant of body tissues under the skin and body impedance in order to switch undetermined multiple frequencies and the measuring signal of dielectric constant of body tissues under the skin. The signal wires of weighing sensor 19 are connected with weighing signal process circuit 18, and the processed signal is applied to one interface of MCU system 20 of the measuring apparatus as a frequency signal through weighing signal processing circuit 18. The determined data by measurement are emitted or received by infrared ray-emitting-receiving circuit 21.

In the present invention, there are four embodiment examples of capacitance grid sensor for measuring the dielectric constant of body tissues under the skin.

Figure 7A:
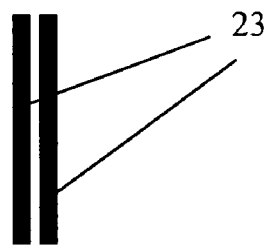
FIG. 7A is a schematic view showing the first kind of electrode configuration of capacitance grid sensor measuring the dielectric constant of body tissues under the skin.

Referring now to FIG. 7A, the two groups of electrodes 25 of the capacitance grid sensor for measuring the dielectric constant of body tissues under the skin are equidistant, and circle outward from the circular or rectangular center, and the two groups of electrodes are never intersectant.

Figure 7B:
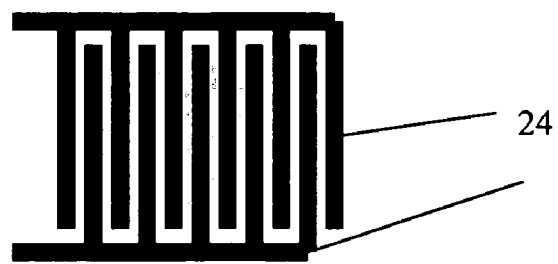
FIG. 7B is a schematic view showing the second kind of electrode configuration of capacitance grid sensor measuring the dielectric constant of body tissues under the skin.
Figure 7C:
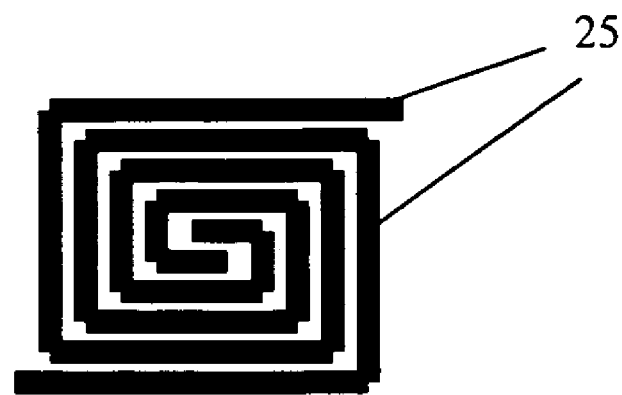
FIG. 7C is a schematic view showing the first kind of electrode configuration of capacitance grid sensor measuring the dielectric constant of body tissues under the skin.
Figure 7D:
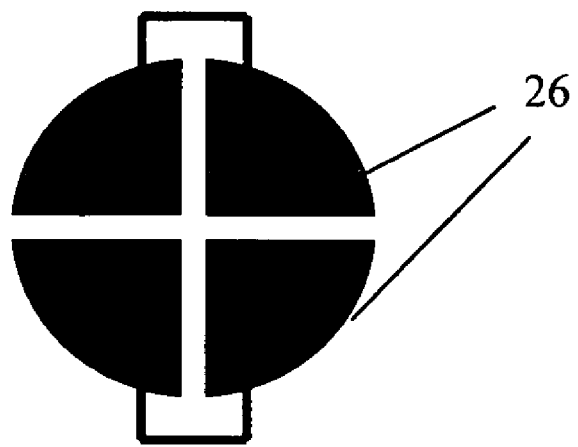
FIG. 7D is a schematic view showing the second kind of electrode configuration of capacitance grid sensor measuring the dielectric constant of body tissues under the skin.

Referring now to FIG. 7B, the electrodes 26 of capacitance grid sensor for measuring the dielectric constant of body tissues under the skin are equidistant and non-touching plates, and are connected by conductors to become two equidistant and non-touching electrode groups.

Figure 8:
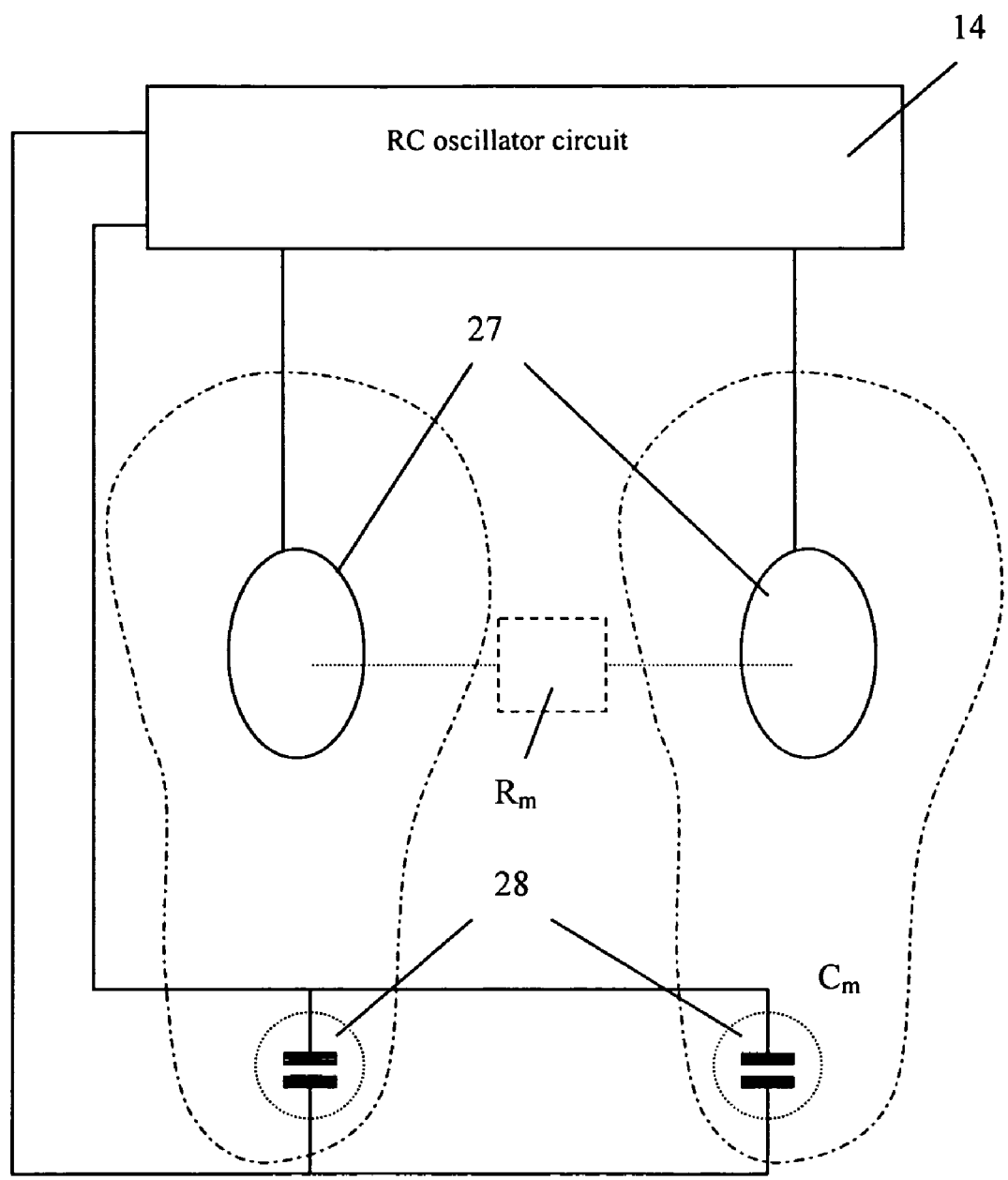
FIG. 8 is a schematic view showing the measuring mode of measuring the dielectric constant of body tissues under the skin and body impedance by applying undetermined frequencies through sole.

Referring now to FIG. 8, it shows a measuring method, wherein the subject is connected to the circuit as an impedance element Rm for measuring body impedance and dielectric constant of body tissues under the skin. The testee's two feet contact two (groups of) electrode plates 27 simultaneously and respectively. Then the human body is connected as a two end impedance element Rm with positive feedback RC oscillator circuit 14 for measuring the dielectric constant of body tissues under the skin and body impedance, and a loop is formed at and below the human body waist place. The oscillating frequency of the oscillator circuit is related to the impedance element Rm. By changing parameters of other elements of oscillator circuit, several different frequency signals are obtained related to body impedances, then the body impedances corresponding to several different frequencies are determined. When the testee's foot soles contact two capacitance grid sensors 28, capacitor Cm is formed, and the positive feedback RC oscillator circuit 14 for measuring the dielectric constant of body tissues under the skin and body impedance connected with Cm generates oscillating frequency signals related to dielectric constant of body tissues under the skin, then this kind of frequency digital signals are dealt with by sampling and the dielectric constant of body tissues under the skin is determined.

Figure 9:
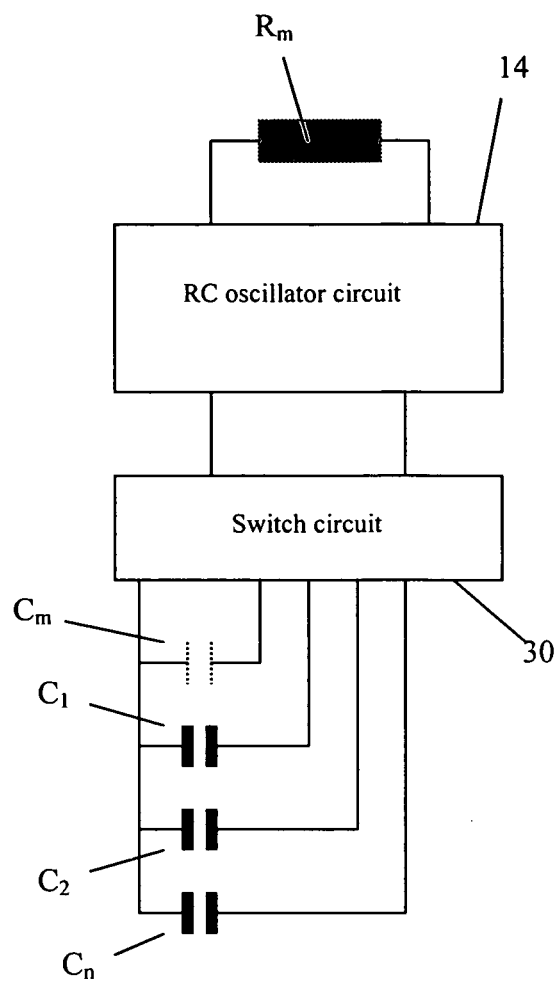
FIG. 9 is a schematic diagram showing the circuit system structure of measuring the dielectric constant of body tissues under the skin and body impedance by using undetermined frequencies.

Referring now to FIG. 9, it shows the system configuration of circuit for measuring dielectric constant of body tissues under the skin and body impedance by using undetermined frequencies. Human body impedance Rm is coupled to the positive feedback RC oscillator circuit 14 for measuring the dielectric constant of body tissues under the skin and body impedance, capacitor Cm formed by capacitance grid sensor together with capacitors C1, C2, ... Cn, which are different in values, are introduced to switch circuit 30. Switch circuit 30 is introduced to the positive feedback RC oscillator circuit 14 for measuring the dielectric constant of body tissues under the skin and body impedance. By switching C1, C2, ... Cn in circuit 30 to the positive feedback RC oscillator circuit 14 for measuring the dielectric constant of body tissues under the skin and body impedance, oscillating signals of multiple undetermined frequencies related to Rm are generated, then body impedances can be measured corresponding to different frequencies. By switching circuit 30 Cm is introduced to the positive feedback RC oscillator circuit 14 for measuring the dielectric constant of body tissues under the skin and body impedance and dielectric constant of body tissues under the skin can be measured. The principle is described as follows:

When C1 is introduced to the positive feedback RC oscillator circuit 14 for measuring the dielectric constant of body tissues under the skin and body impedance, the output frequency of oscillating signal is:

$$f_1 = \frac{K}{R_m C_1}$$

When C1 and Cm are in parallel connection and introduced to the positive feedback RC oscillator circuit 14 for measuring the dielectric constant of body tissues under the skin and body impedance, the output frequency of oscillating signal is $$f_2 = \frac{K}{R_m(C_1 + C_m)}$$

Then can get $$C_m = \frac{C_1(f_1 - f_2)}{f_2}$$

While dielectric constant of body tissue under the skin, $\in_r$, can be gotten by following equation $$\varepsilon_r = \frac{C_m \delta}{\varepsilon_0 A}$$

where δ is the electrode distance of capacitance grid sensor, $\in_0$ is vacuum dielectric constant □A is electrode area forming the capacitance of capacitance grid.

Figure 10:
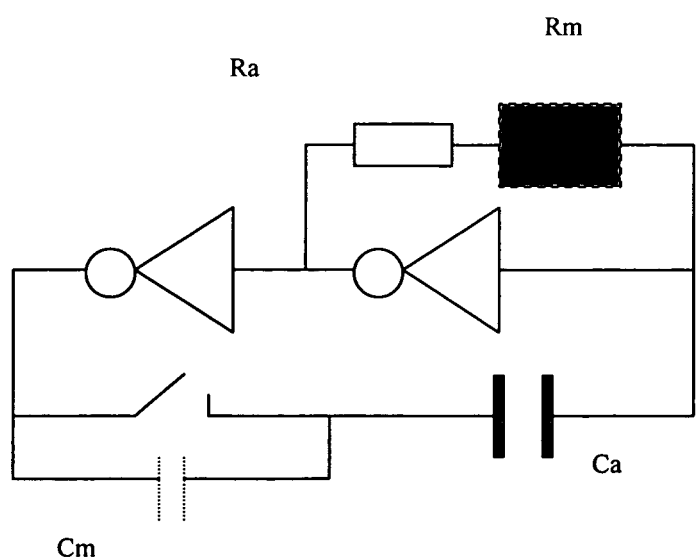
FIG. 10 is a schematic diagram showing the positive feedback RC oscillator circuit for measuring the dielectric constant of body tissues under the skin in the positive feedback RC oscillator circuit for measuring the dielectric constant of body tissues under the skin and body impedance.

Referring now to FIG. 10, it is a schematic view showing the circuit for measuring the dielectric constant of body tissues under the skin in the positive feedback RC oscillator circuit for measuring dielectric constant of body tissues under the skin and body impedance. The circuit is made up of two invertors, capacitor Ca, resistor Ra, body impedance Rm and capacitance grid sensor Cm in contact with human's soles. The connection between capacitance grid sensor Cm and capacitor Ca is in series, and the other ends of the series circuit are respectively connected with the output end of one invertor and input end of the other invertor. The connection between Ra and Rm is in series, and the other ends of the series circuit are respectively connected with the input end and the output end of one invertor. The input end of one invertor is connected with the output end of the other invertor.

Figure 11:
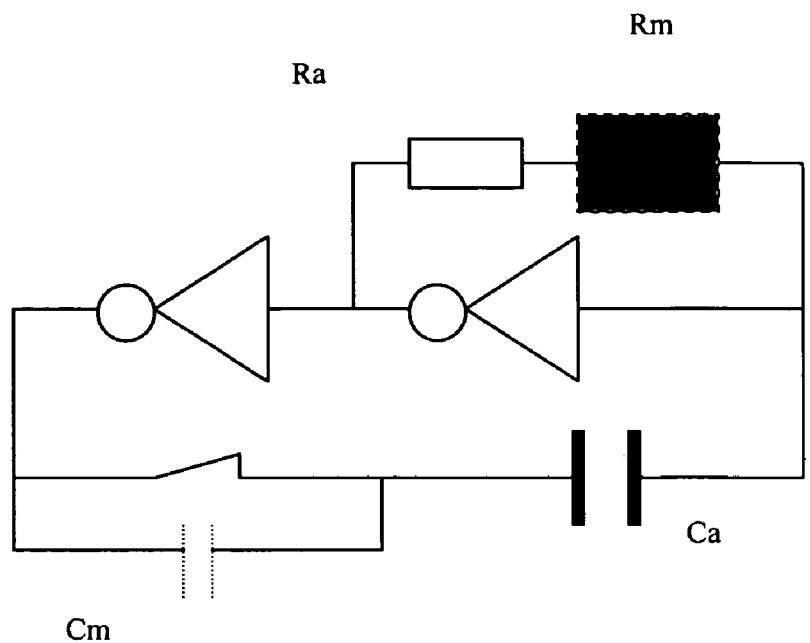
FIG. 11 is a schematic view showing the circuit for measuring the body impedance in the positive feedback RC oscillator circuit for measuring dielectric constant of body tissues under the skin and body impedance.

Referring now to FIG. 11, it is a schematic view showing the circuit for measuring the body impedance in the positive feedback RC oscillator circuit for measuring dielectric constant of body tissues under the skin and body impedance. The circuit comprises two invertors, resistor Ra, capacitor Ca and body impedance Rm. The capacitance grid sensor Cm is a short-circuit capacitance in the circuit. The input end of one invertor is connected with the output end of the other invertor, between the joint of the two invertors and the input end of the invertor, the series-wound circuit comprised by resistor Ra and body impedance Rm is introduced. The two ends of the capacitor Ca are connected respectively with the two invertors' two ends that are not connected with each other. The oscillating frequency of the oscillator circuit can change with the different body impedance Rm.

Figure 12:
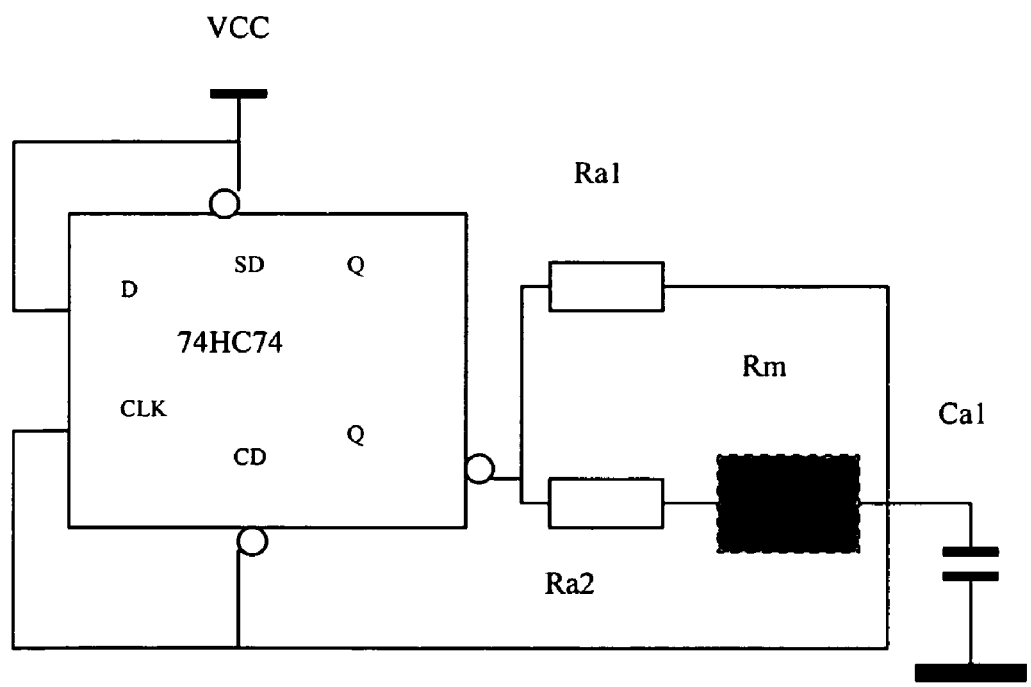
FIG. 12 is an alternative schematic view showing the circuit for measuring the body impedance in the positive feedback RC oscillator circuit for measuring dielectric constant of body tissues under the skin and body impedance.

Referring now to FIG. 12, it is a schematic view showing another kind of circuit for measuring the body impedance in the positive feedback RC oscillator circuit for measuring dielectric constant of body tissues under the skin and body impedance. The circuit comprises one D trigger, resistors Ra1 and Ra2, capacitor Ca1 and body impedance Rm. The body impedance Rm is in series connection with resistor Ra1 and then in parallel connection with resistor Ra2. The one end of the circuit in series-parallel connection is connected with the invert end of the D trigger, and another end is connected with the CD end, CLK end, and GND end of the D trigger. The oscillating frequency of the oscillator circuit can change with the different body impedance Rm.

Figure 6:
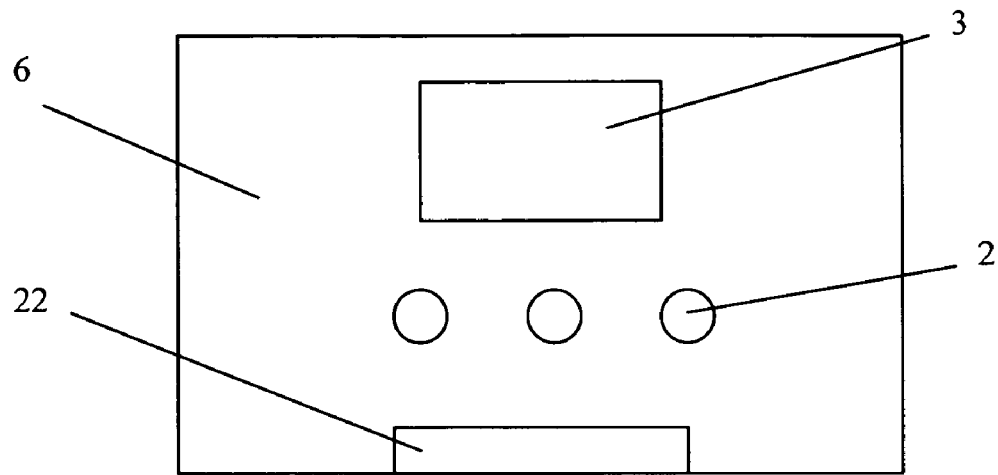
FIG. 6 is a schematic view showing the platform configuration of display apparatus based on the measuring mode shown in FIG. 1B.
Figure 13:
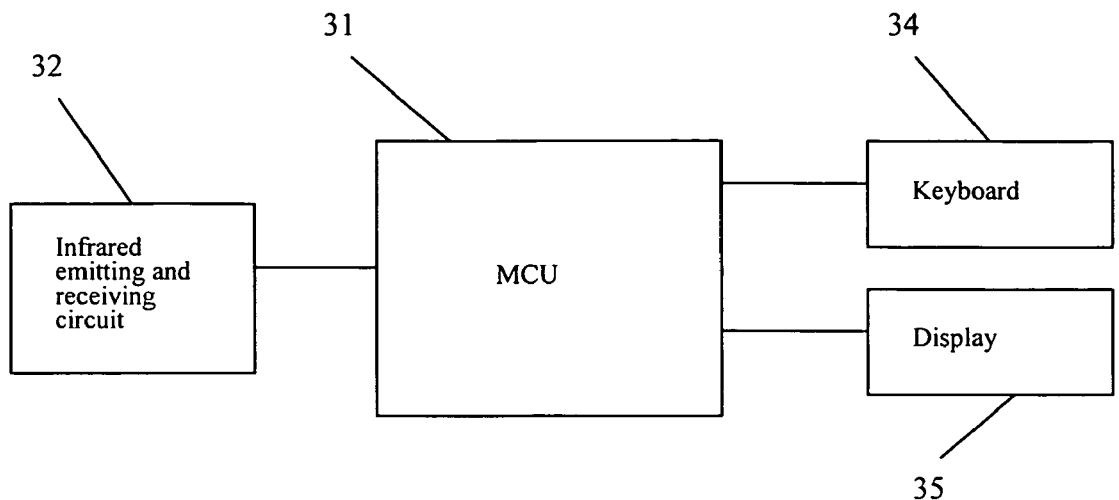
FIG. 13 is a schematic diagram showing circuit structure based on the display apparatus shown in FIG. 6.

Referring now to FIG. 13, it shows the circuit system based upon the display apparatus shown in FIG. 6. Keyboard 34, display 35 and infrared emitting-receiving circuit 32 are all connected with corresponding interfaces of MCU system 31 of the display apparatus.

Figure 14:
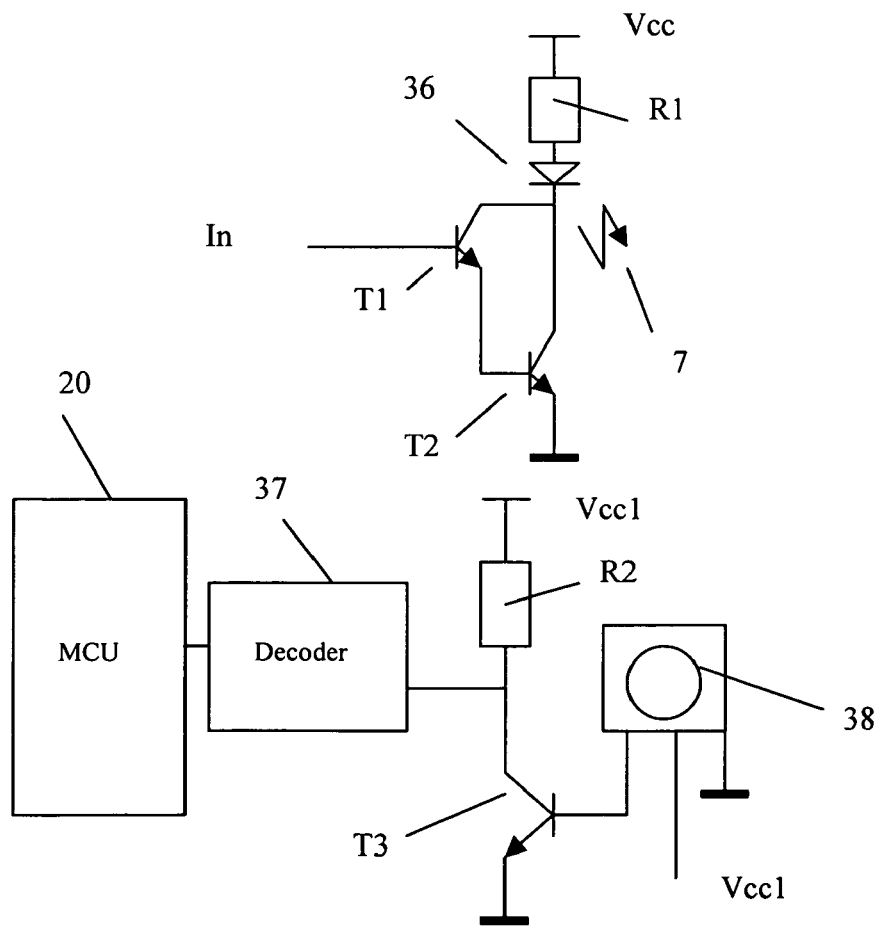
FIG. 14 is a schematic diagram showing the configuration of infrared signal transmitting circuit in measuring apparatus based on the measuring mode shown in FIG. 1B.

Referring now to FIG. 14, it shows the configuration of infrared signal transmitting circuit configuration of measuring apparatus based upon the measuring mode shown in FIG. 1B. Electrical signal is input from the base electrode of audion T1, the collectors of audion T1 and T2 are connected with one port of infrared emitter 36, and the other port of infrared emitter 36 is connected with current-limiting resistor R1, infrared emitter 36 emits infrared data signal 7. Infrared receiver 38 receives the infrared instruction signal emitted by display apparatus when operated, and converts the infrared signal to electrical signal, which is then transmitted from infrared receiver 38 to the base electrode of audion T3. The collector of audion T3 is connected with the input level of decoder 37. The output level of decoder 37 is connected with MCU system 20 of the measuring apparatus. This circuit makes measuring apparatus realize the two-direction transition of infrared signal.

Figure 15:
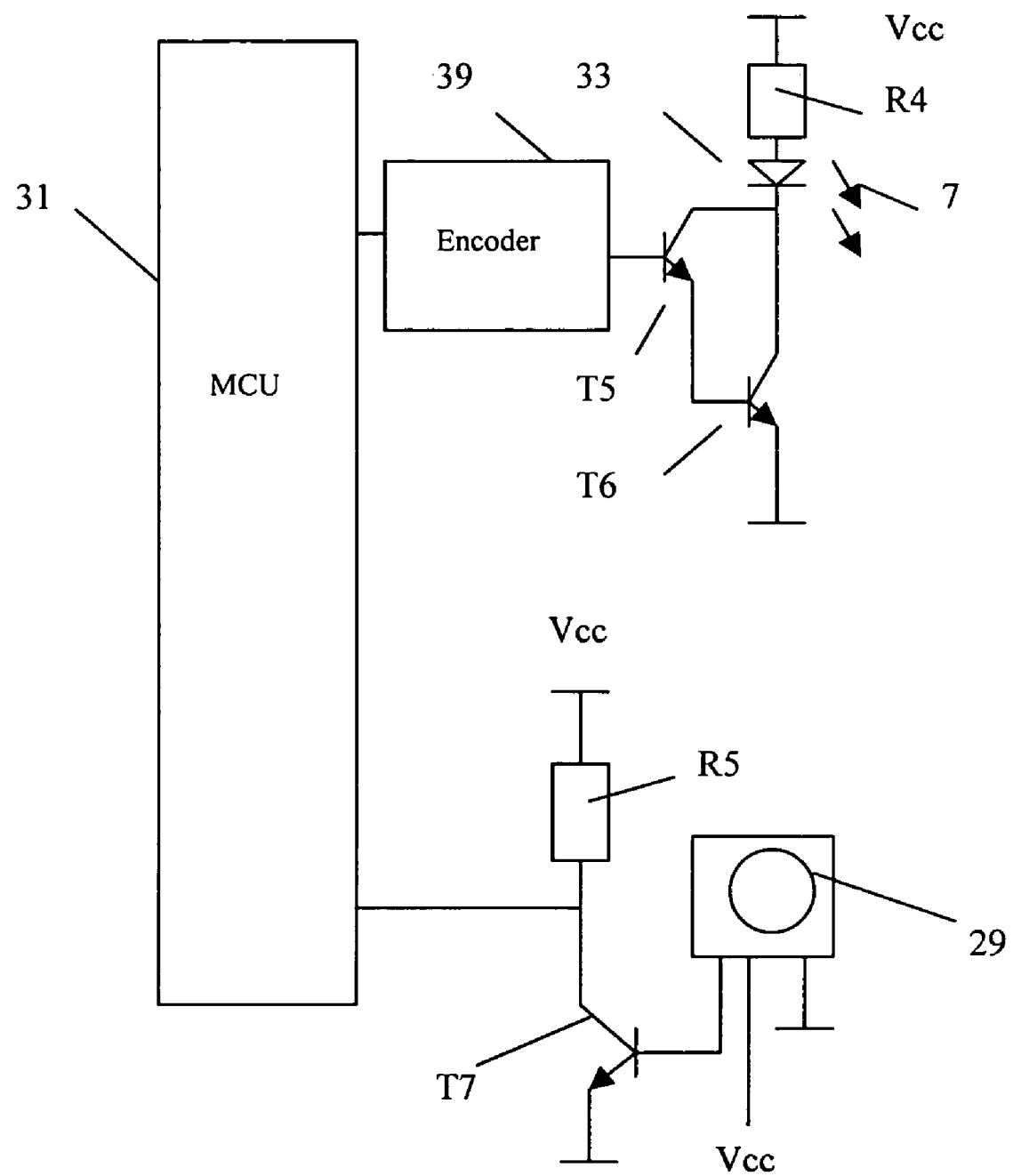
FIG. 15 is a schematic diagram showing the configuration of infrared signal transmitting circuit in display apparatus based on the measuring mode shown in FIG. 1B.

Referring now to FIG. 15, it shows the configuration of infrared signal transmitting circuit in display apparatus. Infrared receiver receives the data signal emitted from measuring apparatus, and the data signal is converted to electrical signal, which is then transmitted from infrared receiver 29 to the base electrode of audion T7. The collector of audion T7 is connected with the interface of MCU system 31 of the display apparatus. The interface of MCU system 31 of the display apparatus sends electrical signal to the input interface of encoder 39, whose output interface is connected with the base electrode of audion T5. The collectors of audion T5 and T6 are connected with one port of infrared emitter 33, and the other port of infrared emitter 33 is connected with current-limiting resistor R4. Infrared emitter 33 emits infrared instruction signal 7. This circuit makes display apparatus realize the two-direction transition of infrared signal.

The advantages of the present invention are: 1. To jointly evaluate body composition by using the two measuring parameters of body impedance by measurement and the dielectric constant of body tissues under the skin measured by the capacitance grid sensor in contact with the human body's skin, so to decrease the uncertainty caused by assessment using only one measured parameter; 2. To measure the body impedance and dielectric constant of body tissues under the skin based on the method of frequency digital sampling, so to leave out the A/D converting part and to improve the measuring accuracy; 3. To measure body impedance by using non-fixed multiple frequency method, so to make the body difference to be indicated more obviously in body impedance difference and to indicate the body composition status genuinely. The apparatus of the present invention is used to conveniently monitor the body composition in everyday life.

What is claimed is:

1. A method for measuring dielectric constant of body tissues under the skin and body impedance based on a method of frequency digital sampling and for evaluating body composition, the method comprising inputting by keyboard a testee's serial number, height, age, gender, and parameter indicating whether or not an athlete; standing a testee with the testee's feet on a measuring platform having a weighing sensor to measure body weight, providing a body weight signal from the weighing sensor to a weighing signal processing circuit; generating oscillating frequency signals related to testee's impedances and dielectric constant of tissues under the skin with a positive feedback RC oscillator circuit and connecting the positive feedback RC oscillator circuit to an MCU system for frequency digital sampling; calculating body fat content and total body water by software of the MCU system, and displaying body weight, body fat content and total body water on the display, wherein said method further comprises:

providing body weight signals from the weighing signal processing circuit as frequency signals;

connecting the positive feedback RC oscillator circuit with two ends of a capacitance grid sensor to generate an oscillating frequency related to dielectric constant of body tissues under the skin by positioning testee's feet soles to contact the capacitance grid sensor on the measuring platform;

connecting the positive feedback RC oscillator circuit with two electrode plates or two groups of electrode plates on the measuring platform, and generating oscillating frequency signals related to body impedance by positioning the testee's feet soles to contact the two electrode plates or two groups of electrode plates within a certain area on the measuring platform;

introducing switched capacitors with different capacitance values to said positive feedback RC oscillator circuit and obtaining several oscillating signals with non-fixed different frequencies related to body impedance;

inputting body weight frequency signals coming from the weighing signal processing circuit, oscillating frequency signals related to dielectric constant of body tissues under the skin and body impedance signals corresponding to the several oscillating signals with non-fixed different frequencies from the switched capacitors through an I/O interface of the MCU system;

calculating from the signals provided to the I/O interface a ratio between intracellular water and total body water through software of the MCU system; and displaying the ratio between intracellular water and total body water.

2. The method for measuring dielectric constant according to claim 1, wherein: one end of the said capacitance grid sensor (Cm) in contact with testee's feet soles is connected with one end of a capacitor (Ca); and other ends of the capacitance grid sensor and capacitor are respectively connected with an output end of one inverter and an input end of another inverter; and the input end of the one inverter is connected with an output end of the another inverter.

3. A method for measuring dielectric constant according to claim 1, wherein: an input end of one inverter is connected with an output end of the another inverter at a connection; and connecting a series-wound circuit comprising a resistor (Ra) and body impedance (Rm) between the connection and an input end of another inverter, and two ends of a capacitor (Ca) are connected respectively with an output end of the one inverter and an input end of the another inverter.

4. A method for measuring dielectric constant according to claim 1, wherein: a body impedance (Rm) is in a series connection with a first resistor (Ra2) and then in parallel connection with a second resistor (Ra1) to form a series-parallel circuit; one end of the series-parallel circuit is connected to an inverting terminal of a D trigger; and the another end of the series-parallel circuit is connected with a CD end, a CLK end, and a GND end of the D trigger.

5. A method for measuring dielectric constant according to claim 1, comprising introducing a body impedance element (Rm) to said positive feedback RC oscillator circuit; switching and introducing a plurality of capacitors to said positive feedback RC oscillator circuit.

6. A body composition monitor apparatus for measuring dielectric constant of body tissues under the skin and body impedance based on a method of frequency digital sampling, the apparatus comprising a measuring unit and a display unit, where the measuring unit and the display unit comprise a measuring platform, a pair of electrode plates, a weighing sensor, a MCU system, a display, and a keyboard; wherein said apparatus also includes a weighing signal processing circuit, a positive feedback RC oscillator circuit for measuring a dielectric constant of body tissue under the skin and body impedance, and a plurality of capacitance grid sensors providing dielectric constant signals of body tissues under the skin to said positive feedback RC oscillator circuit, wherein:

the electrode plates form electrodes for measuring body impedance of a person standing thereon and being connected with said positive feedback RC oscillator circuit to provide an only impedance signal to said positive feedback RC oscillator circuit; and the positive feedback RC oscillator circuit and the weighing signal processing circuit are in electrical connection with a microprocessor of the MCU System.

7. Apparatus according to claim 6, wherein: in one connection mode of said positive feedback RC oscillator circuit for measuring dielectric constant of body tissues under the skin, one end of one capacitance grid sensor (Cm) is connected with one end of a capacitor (Ca); other ends of the one capacitor grid sensor (Cm) and the capacitor (Ca) are respectively connected with an output end of one inverter and an input end of another inverter; a resistor (Ra) is in series circuit connection with a body impedance (Rm), and ends of the series circuit are connected with an input end and the output end of the one inverter; an input end of the one inverter is connected with an output end of the another inverter.

8. Apparatus according to claim 6, wherein: in one connection mode of said positive feedback RC oscillator circuit for measuring body impedance, an input end of one inverter is connected with an output end of another inverter; connecting a series wound circuit comprising a resistor (Ra) and the body impedance (Rm) between the connection of the two inverters and an input end of another inverter; a series-wound circuit comprising a resistor (Ra) and a body impedance (Rm), and ends of a capacitor (Ca) are connected respectively to an output end of the one inverter and an input end of the another inverter.

9. Apparatus according to claim 6, wherein: in one connection mode of said positive feedback RC oscillator circuit for measuring body impedance, a body impedance (Rm) is connected with a first resistor (Ra1) and with a second resistor (Ra2) to form a series-parallel circuit; one end of the series-parallel circuit is connected with an inverting end of a D trigger; and a second end of the series-parallel circuit is connected with a CD end, a CLK end, and a GND end of the D trigger.

10. Apparatus according to claim 6, wherein: including an infrared signal emitter; an electrical signal is input from a base electrode of a first audion (T1); collectors of the first audion (T1) and a second audion (T2) are connected with one port of the infrared emitter; and another port of the infrared emitter is connected with a current-limiting resistor (R1); the infrared emitter emitting a real-time infrared data signal; and an infrared receiver receiving the infrared data signal, which is converted to an electrical signal and transmitted from the infrared receiver to a base electrode of a third audion (T3); a collector of the third audion (T3) is connected with an input level of a decoder; an output level of the decoder is connected with the MCU System.

11. Apparatus according to claim 6, wherein: said display unit includes an infrared emitter comprising an infrared signal transmitting circuit; a receiver receiving the infrared signal and providing an electrical signal that is transmitted from the infrared receiver to a base electrode of a first audion (T7); a collector of the first audion (T7) is connected with an interface of the MCU system of the display unit; the interface of the MCU system of the display unit sends electrical signal to an input interface of an encoder, the encoder having an output interface connected with a base electrode of a second audion (T5); collectors of the second audion (T5) and a third audion (T6) are connected with the infrared emitter; and the infrared emitter is further connected with a current-limiting resistor (R4); whereby the infrared emitter emits infrared instruction signals.

* * * * *

UNITED STATES PATENT AND TRADEMARK OFFICE
CERTIFICATE OF CORRECTION

| | | |
|---|---|---|
| PATENT NO. | : 7,483,735 B2 | |
| APPLICATION NO. | : 10/727677 | |
| DATED | : January 27, 2009 | |
| INVENTOR(S) | : Yan Liu | |

It is certified that error appears in the above-identified patent and that said Letters Patent is hereby corrected as shown below:

In the Claims:
Beginning at Column 11, claim 1, line 5 ending at Column 11, claim 1, line 7 should be:
-- tissues under the skin and body impedance based on frequency digital sampling and for evaluating body composition, a comprising: --

Beginning at Column 11, claim 1, line 19 and ending at Column 11, claim 1, line 21 should be:
-- system, displaying body weight, body fat content and total body water on a display, --

Beginning at Column 11, claim 1, line 24 and ending at Column 11, claim 1, line 24 should be:
-- processing circuit; --

Beginning at Column 11, claim 3, line 64 and ending at Column 11, claim 3, line 64 should be:
-- with an output end of another inverter at a connection; and --

Beginning at Column 12, claim 4, line 10 and ending at Column 12, claim 4, line 10 should be:
-- and a CLK end, of the D trigger. --

Beginning at Column 12, claim 6, line 33 and ending at Column 12, claim 6, line 33 should be:
-- to provide an only impedance to said positive --

Beginning at Column 12, claim 7, line 47 and ending at Column 12, claim 7, line 47 should be:
-- circuit are connected with an input end of the another inverter and the output end of --

Beginning at Column 12, claim 8, line 57 ending at Column 12, claim 8, line 59 should be:
-- and an input end of another inverter; and ends of a capacitor (Ca) are connected respectively to an --

Beginning at Column 13, claim 10, line 2 and ending at Column 13, claim 10, line 2 should be:
-- nected with a CD end, a CLK end of the D --

Signed and Sealed this
Eighteenth Day of October, 2011

David J. Kappos
*Director of the United States Patent and Trademark Office*

CERTIFICATE OF CORRECTION (continued)
U.S. Pat. No. 7,483,735 B2

Beginning at Column 13, claim 10, line 4 and ending at Column 13, claim 10, line 4 should be:
-- 10. Apparatus according to claim 6, further including an --

Beginning at Column 14, claim 11, line 2 and ending at Column 14, claim 11, line 3 should be:
-- unit includes an infrared signal transmitting circuit having an infrared emitter; a receiver receiving the infrared sig- --